United States Patent [19]

Jennings et al.

[11] 4,390,787
[45] Jun. 28, 1983

[54] METHOD AND APPARATUS FOR AUTOMATIC EGG MASS COUNTING

[75] Inventors: Daniel T. Jennings, Orono, Me.; Charles K. Carniglia, Santa Rosa, Calif.; David B. Young, Indian Harbour Beach, Fla.

[73] Assignee: The United States of America as represented by the Secretary of Agriculture, Washington, D.C.

[21] Appl. No.: 202,032

[22] Filed: Oct. 29, 1980

[51] Int. Cl.³ ............................................. G01N 21/33
[52] U.S. Cl. ................................ 250/459.1; 250/461.2
[58] Field of Search .................... 250/461 B, 458, 459, 250/461 R, 372

[56] References Cited

U.S. PATENT DOCUMENTS

| | | | |
|---|---|---|---|
| 3,684,377 | 8/1972 | Adams et al. | 250/461 B |
| 3,918,812 | 11/1975 | Holm | 250/461 B |
| 4,019,060 | 4/1977 | Woodman | 250/461 R |
| 4,162,405 | 7/1979 | Chance et al. | 250/461 B |

FOREIGN PATENT DOCUMENTS 390442 7/1973 U.S.S.R. .......................... 250/461 B

OTHER PUBLICATIONS

Jennings, "Using Black Light to Find Jack-Pine Budworm Egg Masses", USDA, Forest Service Research Note NC-52, 1968.

Acciavatti et al., "Locating Western Spruce Budworm Egg Masses With Ultraviolet Light", USDA, Forest Service Research Note RM-313, 1976.

*Primary Examiner*—Alfred E. Smith
*Assistant Examiner*—Carolyn E. Fields
*Attorney, Agent, or Firm*—M. Howard Silverstein; David G. McConnell

[57] ABSTRACT

A method for UV (ultraviolet) fluorescence counting of selected biological masses, such as egg masses, on foliage samples comprising the steps of: exposing a foliage sample having attached egg masses to UV radiation by a scanning beam; discriminating between the fluoresced light due to the masses and the fluoresced light due to other biological or foliage components; and counting the egg masses based upon the fluoresced light emitted by the egg masses. Also, an apparatus for UV fluorescence counting of egg masses on foliage samples is provided comprising a sample feed means having a test chamber; combined electro-optical sample scanner, fluorescent light divider, and detector; and an electronic signal discriminator and counter for selecting the divided fluorescent light signals emitted by egg masses from the emitted light of other foliage components, to thereby provide a count of the egg masses.

13 Claims, 3 Drawing Figures

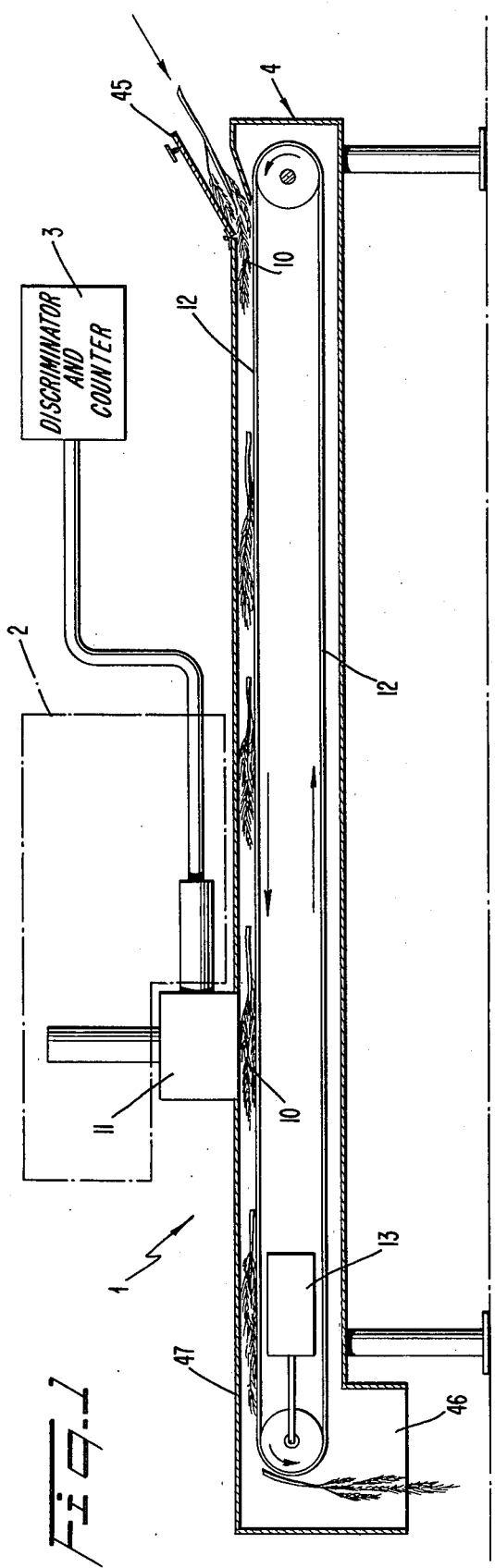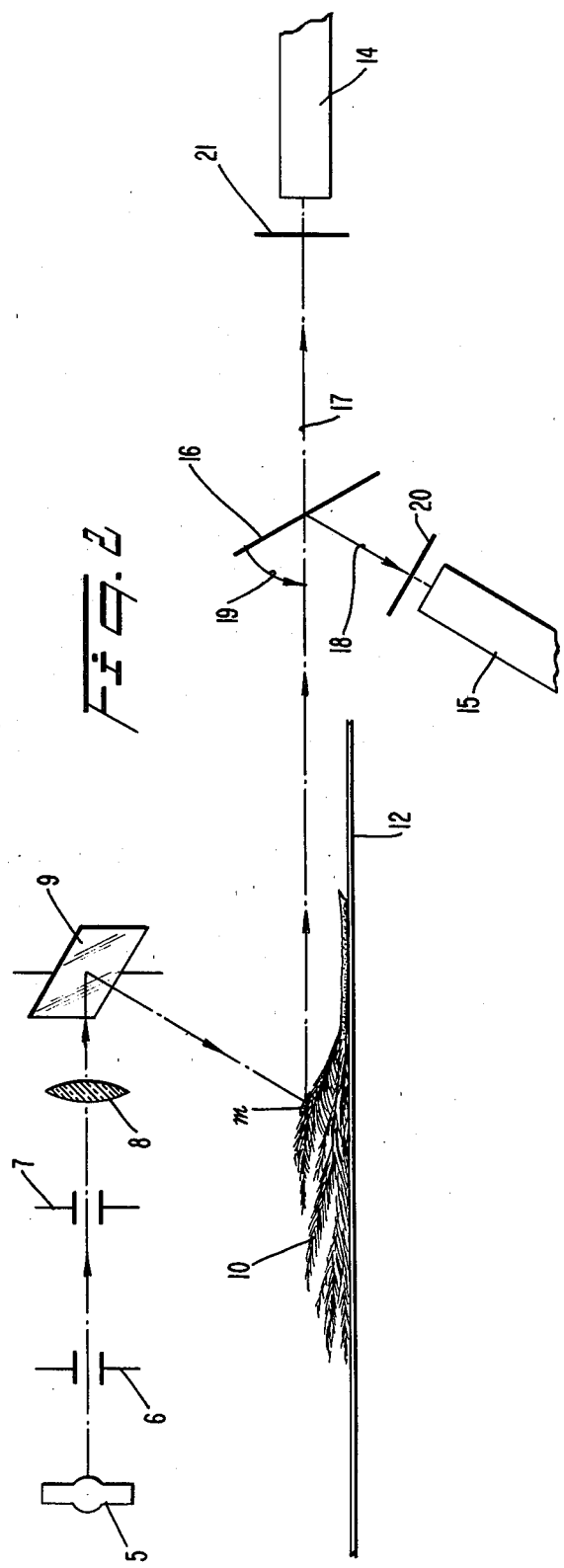

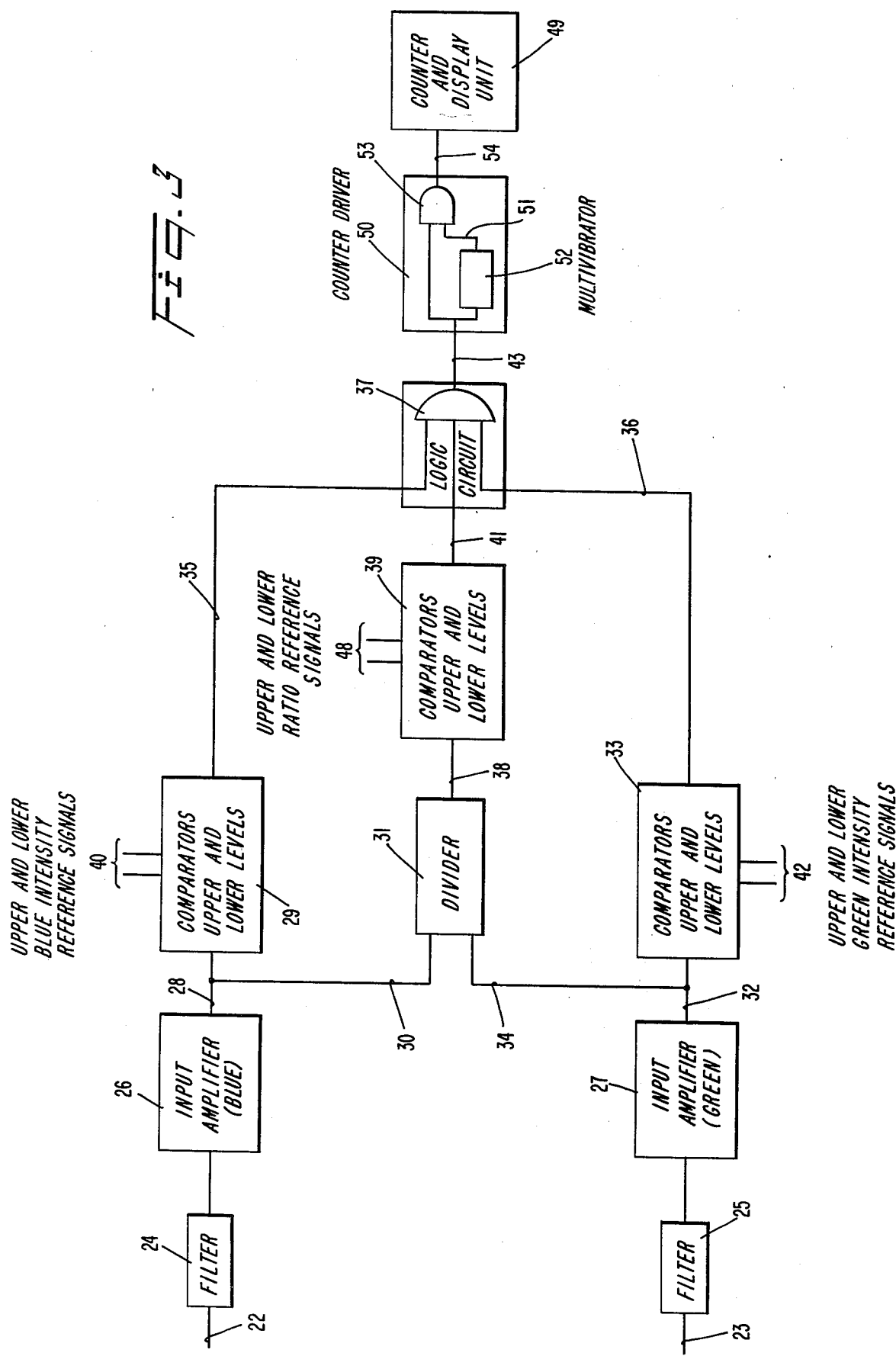

METHOD AND APPARATUS FOR AUTOMATIC EGG MASS COUNTING

BACKGROUND OF THE INVENTION

The invention is in the area of determining the presence of biological masses on foliage. In particular, the invention is directed to a method and apparatus for automatic counting of insect egg masses on foliage samples. The United States has rights in this invention and the patent issued therefor.

Spruce budworm infestations are classified and defoliation predictions are made for the following year based on the number of new egg masses found on host-tree foliage during a current year. In Maine, egg mass surveys for the eastern spruce budworm, *Choristoneura fumiferna* (Clem), are routinely done in mid-July and August. Branch samples are cut from the host balsam fir, *Abies balsamea* (L) Mill., with extendable pole pruners. The branches are then transported to a central laboratory where they are examined visually for budworm egg masses.

The examination process is very tedious and time consuming. The accuracy of finding and counting egg masses may be adversely affected by the budworm population level, nature of the foliage examined, and the worker's experience. Additional factors such as boredom and fatigue tend to further limit accuracy and efficiency.

Daniel T. Jennings, in an article entitled "Using Black Light to Find Jack-Pine Budworm Egg Masses", USDA, Forest Service Research Note NC-56, (1968), discloses that egg masses of the jack-pine budworm (*C. pinus pinus* Freeman) and the eastern spruce budworm (*C. fumiferana* (Clem)) fluoresce when excited by long wave ultraviolet (UV) light. A similar phenomenon was observed for egg masses of the western spruce budworm (*C. occidentalis* Freeman) and was reported in an article by Robert E. Acciavatti and Daniel T. Jennings entitled "Locating Western Spruce Budworm Egg Masses With Ultraviolet Light", USDA, Forest Service Research Note RM-313 (1976). Fluorescence under UV light can aid examiners in locating and counting egg masses more quickly than under ordinary day light illumination. Both studies conclusively demonstrate that accuracy of egg mass examination can be increased by inspection of foliage illuminated by UV light.

When large numbers of foliage samples must be examined for their egg mass content, the problems are greatly multiplied. Even though the improved UV light manual methods require so many man-hours of personnel time to do the actual hands-on counting, most large forest surveying is impracticle. Also, the tedium of manual counting of large samples contributes to even greater inaccuracies in the count due to both mental and physical fatique.

Furthermore, direct exposure to UV light by personnel who do large volume manual counting for an extended period of time, may be undesirable because of possible side effects upon a person's skin and eyes.

SUMMARY OF THE INVENTION

In view of the foregoing, it is an object of the invention to provide a method and apparatus for rapid examination of a large number of foliage samples and counting of biological masses, such as egg masses, requiring a relatively low number of man-hours.

Another object of the invention is to provide a mechanized biological mass counter capable of examining large numbers of foliage samples and counting egg masses with improved accuracy.

Another object of the invention is to provide an apparatus employing UV assisted biological mass counting in which the operator is only minimally exposed to UV radiation.

Additional objects, advantages, and novel features of the invention will be set forth in the description which follows and in part will become apparent to those skilled in the art upon examination of the following or may be learned by practice of the invention. The objects and advantages of the invention may be realized and attained by means of the instrumentalities and combinations particularly pointed out in the appended claims. In its broadast aspects, it will be recognized that this method and the related apparatus, may be applied to determination and counting of many selected biological masses exhibiting flurescence when exposed to UV light. For simplicity, the preferred embodiment will be described only as egg mass counting.

Thus, to achieve the foregoing and other objects and in accordance with the purpose of the invention as embodied and broadly described herein, the method of egg mass counting of the invention comprises the steps of: exposing a foliage sample having attached egg masses to UV radiation in a test chamber; detecting a flurescence emitted by the sample and dividing the fluoresced light into at least one component color; distinguishing (discriminating) between the fluoresced light due to the egg masses and the fluoresced light due to other biological or foliage components; and counting the egg masses based upon the fluoresced light emitted by the egg masses.

Preferably the UV radiation is scanned by a beam onto the foliage samples, and the detected fluoresced light is divided by a beam splitter or filter into blue and green components which are individually measured. By comparing the detected fluorescence of a sample to predetermined low and high levels (obtained by calibration) light not due to egg masses is screened out and does not contribute to the count. While analog discriminator and counting techniques may be employed, digital techniques are preferred.

Preferably, a screened level of blue fluoresced light and a screened level of green fluoresced light and a ratio of a screened level of blue to green fluoresced light are used in counting egg masses on foliage samples. Preferably, the screened level of blue, the screened level of green, and the screened ratio of blue to green are inputted to an AND gate whose output controls a counter and display.

In another aspect of the invention, an automatic egg mass counting apparatus for foliage samples is provided comprising: an electro-optical detector; an electronic discriminator and counter; and a sample feed means having a test chamber.

UV light is scanned by a beam by a rotating mirror onto a foliage sample containing an egg mass. The emitted fluoresced light from the sample is divided into blue and green components by a beam splitter and a filter, and the separated blue and green components are detected and counted separately. By comparing the detected fluorescence of a sample to predetermined low and high levels, light not due to egg masses is screened out.

The sample feed means has entry and exit ports sufficiently far from the test chamber so that extraneous light is prevented from propagating either out from or into the test chamber, thereby excluding exposure of UV light to the operator and excluding spurious signal to the counter.

In both the method and apparatus of the invention, the rate of exposure of the foliage samples to a scanning UV beam is coordinated with the throughput rate of samples through the test chamber so that an optimum egg mass count is obtained. Preferably, the scanning pattern across the sample is such that a series of scanned bands of light beam width are separated by unscanned bands of equal width, i.e. bands also of light beam width.

Thus, by employing the method of egg mass counting of the invention and the apparatus for egg mass counting of the invention, the following benefits result. A large number of foliage samples having attached egg masses can be counted by employing only relatively few man-hours. A mechanized apparatus provides consistency and reproducability of measurement conditions for a large number of foliage samples. The UV fluorescence apparatus is designed so that the operator is exposed only minimally to UV radiation.

BRIEF DESCRIPTION OF THE DRAWING

The accompanying drawings, which are incorporated in and form a part of the specification, illustrate a preferred embodiment of the present invention and, together with the description, serve to explain the principles of the invention. In the drawings:

FIG. 1 is a schematic diagram of an apparatus for carrying out the principles of the invention.

FIG. 2 is a schematic diagram of an electro-optical detector of the invention.

FIG. 3 is a schematic block diagram of an electronic discriminator and counter of the invention.

DETAILED DESCRIPTION OF THE INVENTION

Reference will now be made in detail to the present preferred embodiment of the invention, an example of which is illustrated in the accompanying drawings.

With reference to FIG. 1, in accordance with the invention, the automatic egg mass counter 1 is comprised of: an electro-optical detector 2; an electronic discriminator and counter 3; and a sample feed means 4 having a test chamber 11. In the following paragraphs each of these components is described in detail.

In accordance with the apparatus of the invention, the function of the electro-optical detector 2 is to convert the optical energy being emitted from the various fluorescing components in the foliage sample 10 into electrical signals appropriate for use in electronic discriminating circuitry. In addition, optical detector 2 performs some of the needed signal processing by means of optical filters (or alternately prisms or grating) which separate the blue and green light components from the total spectra being emitted and direct them to the corresponding detectors. The ultraviolet light source is also a part of this detector.

With reference to FIG. 2, the UV light needed is generated by a special light source 5 and directed through a series of control elements which include a brightness control aperture 7, a lens 8, and a filter (not shown) to the rotating mirror 9.

A small aperture or field stop 6 in front of the lamp limits the apparent size of the source. By imaging this field stop with the lens 8, a small spot of light can be focused onto egg mass M of sample 10 in the test chamber 11. This adjustable stop allows a spot (or beam) with a diameter of from 0.7 to 2 mm. to be chosen. Preferably, the stop produces a spot or beam size of 1.4 mm.

A second adjustable aperture or stop 7 is used to control the intensity of the beam by controlling the amount of light which is allowed to enter the sample chamber 11. This stop has no effect on the actual size of the beam.

Preferably, a quartz lens is used because of the higher transmission in the ultraviolet range.

Rotating mirror 9 deflects the light beam through a slit in the test chamber 11 and at the same time produces a sweep or scan across the test chamber 11 for each revolution of mirror 9. As described in greater detail below, and as shown in FIG. 1, the sample 10 is conveyed to the test chamber 11 on conveyor belt 12 of sample feed means 4.

Because of the high scanning speed of the UV beam across the sample conveyor 12 relative to the forward motion of the conveyor, the scan or sweep is essentially orthogonal to the conveyor belt motion. Multiple scans allow the entire sample 10 to be examined and impinge each egg mass 10 as it passes through the sample chamber 11. Variations in the rate at which the UV beam sweeps across the sample chamber is accomplished by varying the speed of the conveyor drive motor 13.

Three types of UV light sweep patterns over the sample 10 can be obtained depending upon the speed of the sweeping light beam. In one case (overlapping) the scanning or sweeping light beam is fast relative to the speed of the conveyor belt 12; in this case, the entire egg mass is scanned and successive light sweeps overlap one another. In a second case (butted) the sweeping light beam is synchronized with conveyor belt speed so that the entire egg mass is scanned, but with no light beam overlap between successive scans. In a third case (spaced) the sweeping light beam is slower relative to the speed of the sample conveyor; in this case, not all of the egg masses on the sample are completely scanned leaving unscanned bands between successive sweeps. By empirical data it has been determined that optimum accuracy in counting is obtained by use of the latter mentioned spaced sweep pattern. This pattern minimizes the tendency of obtaining double counts of the egg masses M on the sample 10.

Preferably, the sweep rate is adjusted so an egg mass is illuminated for at least 20 microseconds, but a more typical value is 50 microseconds. This means the signal frequency is on the order of 20 Kilohertz. The signal is thus enough lower than the noise produced within the detector 2 to allow filtering and high enough to allow the low frequency drift components to be removed. The magnitude of the signal is a measurement of the light intensity emitted by detected egg mass M and varies dependent upon the condition of the egg mass. The pulse of fluoresced light being emitted from the egg mass as it is illuminated by the UV light scanning across it is the signal which is detected by the optical detectors within the detector 2.

Preferably, in accordance with the invention as shown in FIG. 2, the actual detection or conversion from fluoresced light energy to electrical energy is done by two photomultiplier tubes (PMT) 14 and 15 such as RCA 8053 PMTs. These PMTs have a maximum response at 450 nanometers (nm).

In accordance with the invention, the fluoresced light signal discrimination is based on the intensities of the blue and green fluoresced light components. Before the light emitted from the illuminated egg masses reaches the PMTs, it is divided into blue and green components by a beam splitter 16. Preferably, the beam splitter used is a blue (additive) dichroic filter. Used at normal incidence angle, it passes blue light 17 of wavelength of less than 500 nm while reflecting most of the red and green light 18. As used with an incidence angle 19 close to 45°, the filter transmits blue light and reflects green. Additional filters 20 and 21 are used in front of both PMTs to insure that the unwanted light components passed or reflected by beam splitter 16 at reduced intensities are attenuated still more and that stray light components reflecting from various other objects within the sample chamber 11 are eliminated.

A 2A filter (not shown) is added to block UV light from the PMT. In addition, though not shown in FIG. 2, a shutter system is located in front of each PMT to protect the sensitive face during the adjustment or repair.

In accordance with the invention, the electronic discriminator and counter 3 receives electrical signals from the detector 2, processes them, determines if the signal nature indicates the presence of an egg mass M and, if so, provides a visual indication and/or a registered count.

In accordance with the invention, three conditions must be satisfied before the electronic dicriminator and counter 3 indicated that a fluorescing source is an egg mass M. These conditions are: (a) the magnitude of the signal from the blue channel PMT must be within specified limits; (b) the magnitude of the signal from the green channel PMT must be within specified limits; and (c) the ratio of the blue channel signal to that from the green channel signal must fall within specified limits. The actual limits indicated are dependent upon the relative sensitivities of the particular PMT actually installed in each channel and are determined by calibration.

As shown in FIG. 3, in accordance with the invention, incoming signals 22 and 23 corresponding to the intensities of the blue 22 and green 23 light components, are preferably first passed through filters 24 and 25 to remove the high frequency noise signals generated internally by the PMTs and the low frequency signals due to drift in the power supplied and changes in tube characteristics caused by variations in ambient conditions. The filtered signals (in millivolts) are amplified to levels (in volts) usable by the rest of the circuitry allowing commercially available instrumentation amplifiers 26 and 27 to be used. The amplifiers 26, 27 have high input impendance to reduce the loading effects on the PMT circuits. The amplification factor or gain of these units is adjustable and thus may be changed to compensate for differences in PMT sensitivities should these be so disparate that they cannot be compensated by using the other calibration adjustments. As is standard, each amplifier 26 and 27 is provided with a zero adjustment on one input to allow an initial adjustment to near zero output with no input. This setting is a one time adjustment to be done at the beginning of each counting season and whenever an amplifier is replaced.

The amplified signals at the outputs 28, 32 of these amplifiers are used in the discrimination process. The output 28 from the blue channel amplifier is directed to a pair of blue level comparators 29 (for simplicity shown as one block 29) and to the numerator input 30 of the divider 31. The green channel signal 32 is directed to a similar part of comparators 33 (for simplicity shown as one block 33) and to the denominator input 34 of the divider 31. In each case the amplifier output is filtered before being sent to each unit to remove any high frequency components produced by inductive pick-up. This is especially important for the divider inputs since dividers are especially sensitive to high frequency signals.

Two signal level comparators are used for each color component signal to determine whether or not the signal magnitude is within the specified lower and upper limits. Each threshold level is individually adjustable and these adjustments are determined during the calibration. Note that for each of the pairs of comparators 29, 33, there are a pair of upper and lower reference signals supplied; these are respectively reference signals 40 and 42. By varying these levels, differences in PMT sensitivity may be partially reduced, and the counter may be adjusted to detect and count all egg masses or only new egg masses. Up to this point in the circuitry, all signals have been analog or continuous. The output from the comparators 29 and 33, however, is a binary signal.

If the input signals are within the limits set, the comparators outputs 35 and 36 are "1" or "on", otherwise the outputs are "0" or "off". These "off" or "on" signals are the inputs to the binary AND gate 37 which gives an output only when all the input signals are "on". These signals correspond to the decisions (discriminations) regarding the levels of the blue and green signals which in turn correspond to measures of the intensities of the blue and green light components emitted by the fluorescing egg masses.

The output 38 from divider 31 is analog and is a measure of the ratio of the blue light intensity to that of the green light. Because of the characteristics of divider circuits, the two intensity signals have been adjusted using the amplifier gain to make the ratio for a decision to be near unity. In a manner similar to that for the blue and green intensity signals, the ratio signal is fed to a pair of comparators 39 (for simplicity shown as one block 39) with reference signals 48 for the level decision process, and the binary signal at output 41 from the comparators 39 are combined with the signals from outputs 35 and 36 from the level comparators 29 and 33 in the AND gate 37.

In accordance with the broadest aspects of the invention, the blue and green light ratio can be obtained alternatively by digital division of the blue intensity by the green intensity where both the blue and green intensities are obtained by digital techniques. This simply requires that the analog signals be converted to binary signals using analog to digital converters.

In accordance with the invention, a count signal at output 43 is sent to counter driver 50 and then to the counter and display unit 49 only when all comparator output signals 35, 36 and 41 are "on" indicating that all conditions for egg mass detection have been satisfied. This count signal 43 is the output from the binary AND gate 37.

Count signal 43 enters counter driver 50 and is amplified to a count signal of sufficient amplitude for driving the counter and display 49. In counter driver 50, the signal in output 43 and the signal in output 51 of multivibrator 52 are inputted into AND gate 53 to provide signal in output 54 driving counter and display unit 44. Multivibrator 52 serves to block the counter signal for a specified time to avoid multiple counts from the same target egg mass. Multivibrator 52 is adjustable allowing for variation in the blanking time for blocking the counter. Before the signal in output 54 reaches the unit 44, it may be filtered and reshaped by a wave shaping network (not shown) to produce an electrically clean signal, thus reducing the possibility of obtaining false counts due to extraneous noise pulses produced as a result of divider instability or to power lines transients. The actual count is indicated in light emitting diode (LED) characters and entered into a suitable register.

The amplifiers 26 and 27 may be Model 3662 of Burr-Brown of Tucson, Ariz. The comparators 29, 33, and 39 may be Burr-Brown models 4032/12, 4082/03, 4022/25, and 4115/04. The divider 31 may be model 436 of Analoy Devices, Norwood, Mass. A suitable counter and display unit 44 is model DM 3000 of Datel Systems, Inc.

As shown in FIG. 1 and as briefly discussed above, the sample feed means 4 includes a conveyor belt 12 which moves the branch samples 10 through the sample chamber 11 under the UV light beam sweep at a constant known rate to permit repeatable counting results. Branch samples are fed continuously into an entry port 45 at one end by hand discharged from an exit port 46 at the other end after passing through sample chamber 11.

The conveyor 12 may be fabricated from any suitable non-fluorescing material and is preferably a continuous black cloth belt. A variable speed drive motor 13 permits various belt speeds which, when used in conjunction with the UV light beam scan, produces the various sweep patterns (overlapping, butted, and spaced) mentioned above.

Except for the entry port 45 and the discharge port 46, the cover 47 for the conveyor 12 is light-tight. The cover is designed with extended length beyond the end of the testing chamber 11 to prevent the light entering the ports from being able to enter the test chamber 11 by propagating down the conveyor. No additional light traps are needed.

This sample feed means also prevents UV light in the test chamber from propagating out of the test chamber to expose an operator feeding samples into entry port 45 to UV radiation. Preferably, the samples are hand fed through the sample chamber 11 to be scanned and counted, and are then discharged through port 46 on the underside of the enclosure. The samples 10 may be fed as fast as possible onto the moving belt 12 provided enough care is taken to insure that there are no overlapping samples and that each sample is placed so that the top of the foliage faces the scanning UV light beam. Samples should be prepared prior to feeding so that no part of the branch is more than 5 centimeters above the belt surface since the preferred beam focus is designed to concentrate the light in this range.

In its present configuration, the egg mass counter has the flexibility to be calibrated to detect or count only new egg masses (egg masses collected during the same season they were laid) or to detect and count all egg masses. New egg masses are fluffy and white. In their natural state, egg masses are laid on a needle. The needle contributes only a negligible amount to the fluorescence. Data for new egg masses indicates a relatively high level of fluorescence and a preponderance of blue light. Old egg masses are masses that have weathered a year or more before being collected. They are generally flat and ragged in appearance. The old masses have lower fluorescence levels.

Parasitized or partially parasitized egg masses have lower fluorescence levels than new egg masses; completely parasitized egg masses have much lower levels than new egg masses. With few exceptions, buds or pitch droplets exhibit lower fluorescence levels than egg masses. Most of such samples have a preponderance of green fluorescent light.

Bark has a much lower fluorescence level than egg masses. Staminate flowers were measured as they occurred on branches. All had intensities and ratios outside the egg mass range.

Green needles are much dimmer than egg masses. Brown needles usually have a higher fluorescence than green needles. Also, the lower surfaces of green needles show a higher level of fluorescence than the upper surfaces.

In another comparison of manual egg mass counting methods with an automatic egg mass counting method and apparatus according to the invention, manual processing of 477 branch samples required 14,067 minutes for a mean processing time of 29.49 minutes. Automatic processing of the same 477 branch samples required 4,127 minutes for a mean time of 8.65 minutes. The great economy in time of employing the automatic egg mass counter of the invention is apparent.

In view of the foregoing, it is apparent that by employing the method of egg mass counting of the invention and the apparatus for automatic egg mass counting, several benefits result. A large number of foliage samples 10 having attached egg masses M can be examined and egg masses can be counted by employing relatively few manhours. A mechanized apparatus is used which provides consistency and reproducability of measurement conditions for a large number of foliage samples. The UV fluorescence apparatus is designed so that the operator is exposed only minimally to UV radiation. The apparatus can be used as a detector and/or counter of egg masses. For large sample counts, the time spent counting each sample by the automatic egg mass counter is considerably less than the time spent for each sample counted by manual means.

The foregoing description of the preferred embodiment of the invention has been presented for purposes of illustration and description. It is not intended to be exhaustive or to limit the invention to the precise form disclosed, and obvious modifications and variations are possible in light of the above teaching. For example, instead of using vacuum tube photomultiplier tubes (PMT), semi-conductor diodes can be employed. Instead of using analog circuitry for detecting fluoresced light intensity, a digital microprocessor can be used. Furthermore, by changing optical filters and by appropriate recalibration, it may be possible to isolate signals produced by other biological components of interest in a foliage sample or to detect or measure other egg mass conditions, such as their age or health. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for counting biological masses on foliage samples comprising the steps of:
    exposing a foliage sample having attached biological masses to ultraviolet radiation in a test chamber, causing said foliage sample and masses to fluoresce;
    dividing the fluoresced from the exposed biological masses and foliage into blue and green component colors and individually measuring each color;
    discriminating between the fluoresced light due to the biological masses and the fluoresced light from other foliage components; and
    counting the biological masses based upon the fluoresced light of said component colors emitted from the masses.

2. A method for counting biological masses on foliage samples as described in claim 1 wherein is provided the foliage sample moving through the test chamber and simultaneously exposing the sample to a scanning ultraviolet beam of light.

3. A method for counting biological masses on foliage samples as described in claim 2 wherein the rate of throughput of the foliage samples through the test chamber is coordinated with the scanning rate of the UV beam of light.

4. A method for counting biological masses on foliage samples as described in claim 3 wherein the rate of throughput of the foliage samples through the test chamber is coordinated with the scanning rate of the UV beam such that the scanning pattern across the sample is a series of scanned bands of light beam width separated by equal unscanned bands.

5. An automatic biological egg mass counting apparatus for foliage samples, comprising:
    sample feed means having a test station;
    an electro-optical detecting means for detecting fluoresced light having a source of a scanning UV beam of light for scanning foliage samples having biological masses;
    means for detecting light fluoresced from the biological masses on the sample, said means comprising
    a beam splitter means to divide out green and blue light components,
    separate detectors for green and blue light components, and
    electronic discriminator and counting means for discriminating between fluoresced light due to selected biological masses and fluoresced light due to other foliage components.

6. An automatic biological mass counting apparatus for foliage samples as described in claim 5 wherein said source of a scanning UV beam is a rotating mirror.

7. An automatic biological mass counting apparatus as described in claim 5 wherein said sample feed means has an entry port and an exit port sufficiently far from said test chamber so as to prevent light from propagating either out from or into said test chamber.

8. An automatic biological mass counting apparatus as described in claim 5 wherein said electronic discriminator and counting means includes color signal comparators set for screening out low signal intensities and high signal intensities outside of a predetermined color signal intensity band representative of signals due to fluorescence from egg masses.

9. A method for counting biological masses on foliage samples comprising the steps of:
    exposing a foliage sample having attached biological masses to ultraviolet radiation in a test chamber, causing said foliage sample and masses to fluoresce;
    dividing the fluoresced light from the exposed biological masses and foliage into two component colors and individually measuring each color;
    discriminating between the fluoresced light due to the biological masses and the fluoresced light from other foliage components; and
    counting the biological masses based upon the fluoresced light of said component colors emitted from the masses, wherein a screened level of one color and screened level of said other color and a ratio of said one color to the other color are employed to determine said biological mass count.

10. A method for counting biological masses on foliage samples as described in claim 9 wherein said biological masses comprise egg masses and said two component colors are blue and green.

11. A method for counting biological masses on foliage samples as described in claim 10 wherein the detected fluoresced blue and green light is compared to predetermined low and high levels in order to screen out light not due to egg mass fluorescence.

12. A method for counting biological masses on foliage samples as described in claim 11 wherein the screened levels of blue light and screened levels of green light and a screened level of a ratio of blue to green light are employed for determining the egg mass count.

13. A method for counting biological masses on foliage samples as described in claim 12 wherein is provided processing said screened levels in an AND gate having inputs derived from (a) screened level of blue light, (b) screened level of green light, and (c) screened level of ratio of blue to green light; and wherein the output of said AND gate provides the egg mass count.

* * * * *